US009507913B2

(12) United States Patent
Mansi et al.

(10) Patent No.: US 9,507,913 B2
(45) Date of Patent: Nov. 29, 2016

(54) DATA DRIVEN REDUCTION OF MULTI-SCALE MODELS

(71) Applicant: Siemens Aktiengesellschaft, Munich (DE)

(72) Inventors: Tommaso Mansi, Plainsboro, NJ (US); Dorin Comaniciu, Princeton Junction, NJ (US); Bogdan Georgescu, Plainsboro, NJ (US); Ali Kamen, Skillman, NJ (US)

(73) Assignee: Siemens Healthcare GmbH, Erlanger (DE)

( * ) Notice: Subject to any disclaimer, the term of this patent is extended or adjusted under 35 U.S.C. 154(b) by 377 days.

(21) Appl. No.: 14/157,809

(22) Filed: Jan. 17, 2014

(65) Prior Publication Data

US 2014/0207715 A1 Jul. 24, 2014

Related U.S. Application Data

(60) Provisional application No. 61/754,991, filed on Jan. 22, 2013.

(51) Int. Cl.
*G06F 19/00* (2011.01)
*G06F 17/50* (2006.01)
*G06N 99/00* (2010.01)

(52) U.S. Cl.
CPC ......... *G06F 19/3437* (2013.01); *G06N 99/005* (2013.01); *G06F 17/5009* (2013.01)

(58) Field of Classification Search
None
See application file for complete search history.

(56) References Cited

U.S. PATENT DOCUMENTS

2002/0091666 A1* 7/2002 Rice ....................... G06N 3/004
2011/0273558 A1* 11/2011 Subbiah .................... G01J 3/02 348/89
2012/0290521 A1* 11/2012 Frank ................... G06N 99/005 706/45
2013/0103624 A1* 4/2013 Thieberger ........... G06N 99/005 706/12
2014/0108842 A1* 4/2014 Frank ...................... G06F 17/28 713/323
2014/0372348 A1* 12/2014 Lehmann ............. G06K 9/6265 706/12

OTHER PUBLICATIONS

Bassingthwaite et al, The Cardiac Physiome: perspectives for the future, 2009.*
Boriek et al, Desmin integrates the three-dimensional mechanical properties of muscles, 2001.*
Tresch et al, Matrix Factorization Algorithms for the Identification of Muscle Synergies: Evaluation on Simulated and Experimental Data Sets, 2006.*

* cited by examiner

*Primary Examiner* — Stanley K Hill
*Assistant Examiner* — Mikayla Chubb

(57) ABSTRACT

A method of computing physiological measurements resulting from a multi-scale physiological system using a data-driven model includes generating a database of physiological measurements associated with a multi-scale physiological system. A computer uses dimensionality reduction techniques on the database to identify a reduced set of components explaining the multi-scale physiological system. The computer learns a data-driven model of the multi-scale physiological system from the database. Then, new input parameters are received by the computer and used to compute new physiological measurements using the data-driven model. New derived physiological indicators are computed by the computer based on the reduced set of components. Once computed, the new derived physiological indicators may be displayed along with the new physiological measurements.

18 Claims, 5 Drawing Sheets

DATA DRIVEN REDUCTION OF MULTI-SCALE MODELS

This application claims priority to U.S. provisional application Ser. No. 61/754,991 filed Jan. 22, 2013 which is incorporated herein by reference in its entirety.

TECHNICAL FIELD

The present invention relates generally to computer-implemented systems, methods, and apparatuses which may be applied to complex, multi-scale models to automatically identify and reduce the number of relevant parameters and to learn them in order to increase the computational efficiency of the models while preserving their accuracy.

BACKGROUND

Advances in experimental protocols, in particular at the sub-cellular level, and in computational modeling of organ physiology, like the heart for instance, enable the investigation of functional relationships between sub-cellular mechanisms and organ function. For example, the output of detailed sub-cellular models that describe the molecular pathways involved in cardiac myocyte function may be linked to a multi-scale, continuum framework to compute the impact of these pathways at an organ level. However, such detailed models typically rely on numerous algebraic or ordinary differential equations, which may span several temporal and spatial scales. Consequently, these models are computationally demanding and are controlled by a large number of parameters whose direct influence at the organ level, where clinical observations are usually available, is not easily observable. For these reasons, it is challenging to personalize these models, for example, to specific genetic groups, populations, or individual patients.

Various model reduction techniques that rely on statistical learning have been investigated, in particular in the chemometrics community. Often referred to as meta-modeling, these techniques aim to derive a statistical model that is able to capture the output of complex, non-linear computational models while being expressed with fewer parameters. Such models have been used not only to analyze the interactions between parameters, but also to estimate the parameters using libraries of models. Additionally, in the computer vision and medical imaging domain, manifold learning techniques have been applied to reduce the dimensionality of multi-dimensional spaces so that the corresponding data can be visualized. However, these techniques conventionally have been limited to their respective domains and have not been combined, or otherwise extended, to address the challenges of computational complexity and personalization that are associated with modeling heart function. In particular, they have not been applied so far to reduce the complexity of a known multi-scale model.

Accordingly, it is desired to develop a model reduction strategy that may be applied to multi-scale cardiac modeling to reduce the number of parameters of such models and to learn data-driven generative models suitable for simulations which capture the output of their original, corresponding multi-scale models. Such a model would allow fast, patient-specific multi-scale computation.

SUMMARY

Embodiments of the present invention address and overcome one or more of the above shortcomings and drawbacks, by providing methods, systems, and apparatuses for identifying the clinically observable parameters of a multi-scale model, reducing their number, and learning data-driven generative models suitable for simulations which capture the output of the original multi-scale model. The method herein described is illustrated on the heart organ, but could be applied on any multi-scale system, being physiological (e.g., other organs) or systemic (e.g., population, environment). The technology is particularly well-suited to, but not limited to, multi-scale cellular models of cardiac myofilament (MF) and learning data-driven generative models suitable for cell-to-organ simulations.

According to some embodiments of the present invention, a method of computing physiological measurements resulting from a multi-scale system using a data-driven model includes generating a database of physiological measurements associated with a multi-scale physiological system. The computer uses dimensionality reduction techniques on the database to identify a reduced set of components explaining the physiological system. Then, the computer learns a data-driven model of the multi-scale physiological system from the database. After receiving new input parameters, the computer may compute new physiological measurements from the new input parameters, using the data-driven model. The computer may then compute new derived physiological indicators based on the reduced set of components. In some embodiments, the new physiological measurements and/or the new derived physiological indicators may then be displayed.

The database used in the aforementioned method may vary according to different embodiments of the present invention. For example, in one embodiment, the database comprises experimental measurements of the physiological system. In another embodiment, the database is generated by a simulation-based technique. First a number of simulations and a sampling rate are selected. Then, a training data creation process is performed a number of times equal to the number of simulations. This training data creation process may comprise, for example, determining a plurality of unique input parameters; using the unique input parameters, sampling rate, and a multi-scale model of a respective physiological item associated with the multi-scale physiological system to calculate a plurality of values associated with the respective physiological item; and adding the calculated values to the database.

Various dimensionality reduction techniques may be used with the aforementioned method of computing multi-scale, physiological measurements. For example, in some embodiments, the reduced set of components may be identified by applying a manifold learning technique to the database to identify the reduced set of components. In one embodiment, the manifold learning technique is Principle Component Analysis (PCA) and the reduced set of components comprises PCA coefficients. In another embodiment, the manifold learning technique is Locally Linear Embedding (LLE) and the reduced set of components comprises embedding coordinates.

Various techniques may be used for learning the data-driven model of the physiological system from the database in the aforementioned method. For example, in some embodiments, the data-driven model is learned between input parameters and a reduced representation of the physiological measurement. If one or more related physiological measurements are used as input, they may be projected onto a manifold space to yield a reduced representation of each related physiological measurement. In these embodiments, the data-driven model may be a statistical model relating the new input parameters and the reduced representation of the one or more related physiological measurements with the new physiological measurements.

In other embodiments, the data-driven model can be used for dynamic physiological systems. For example, if related physiological measurements are needed as input, a plurality of related physiological measurement values corresponding to times between a start time value and a current time value are received and a subset of simulated related physiological measurement vectors from the database is selected. Various techniques may be used for identifying and/or selecting simulated related physiological measurements. For example, in some embodiments, the subset of simulated related physiological measurement vectors are selected from the database by first, for each simulated related physiological measurement vector in the database, determining a distance value between a respective related simulated physiological measurement vector and the received related physiological measurement values between the start time and the current time value. Next, a predetermined number of simulated related physiological measurement vectors in the database are identified as being closest to the received related physiological measurement values based on their respective determined distance values. Then, the predetermined number of simulated related physiological measurement vectors is designated as the selected subset of related physiological measurement vectors.

Once the simulated related physiological measurement vectors are identified and/or selected, an interpolated related physiological measurement vector may be created based on the subset of simulated physiological measurement vectors and projected onto a manifold space to yield a plurality of related physiological measurement manifold coefficients. For example, the interpolated related physiological measurement vector may be created based on the subset of simulated related physiological measurement vectors by a process comprising two steps. First, an interpolated related physiological measurement vector is determined by interpolating the subset of the simulated related physiological measurement vectors over a heart cycle, weighting each of simulated related physiological measurement vectors in the subset of simulated related physiological measurement by its respective distance value. Then, interpolated related physiological measurement values in the initial interpolated related physiological measurement vector between the start time value and the current time value are replaced with corresponding measured related physiological measurement values included in the measured related physiological measurement to yield the related physiological measurement vector.

The related physiological measurement manifold coefficients created using the interpolated related physiological measurement vector may be used to compute the new multi-scale physiological measurements. For example, in one embodiment, the new multi-scale physiological measurement is computed by applying the data-driven model to the related physiological measurement manifold coefficients and the new input parameters to yield a plurality of output physiological measurement manifold coefficients and determining the new multi-scale physiological measurement based on the output physiological measurement manifold coefficients.

Other embodiments of the present invention include articles of manufacture and systems for computing multi-scale, physiological measurements. For example, in some embodiments, an article of manufacture comprising a non-transitory computer-readable medium holding computer-executable instructions may perform the aforementioned method for computing multi-scale, physiological measurements using a data-driven model, potentially with one or more of the variations noted above. In another embodiment, a system comprising a receiver module, a database, and a modeling processor may be used to compute multi-scale, physiological measurements using a data-driven model. In such embodiments, the receiver module may be configured to receiving new input parameters and the database may be configured to store physiological measurements associated with a physiological system. Then, the modeling processor may be configured to use dimensionality reduction techniques on the database to identify a reduced set of components explaining the multi-scale physiological system; learn a data-driven model of the multi-scale physiological system from the database; receive new input parameters; compute new physiological measurements from the new input parameters, using the data-driven model; compute new derived physiological indicators based on the reduced set of components; and display at least one of the new physiological measurements and the new derived physiological indicators.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

The following disclosure describes the present invention according to several embodiments directed at methods, systems, and apparatuses for automatically identifying relevant parameters of a multi-scale model, reducing the number of such parameters, and learning a data-driven generative model suitable for simulations while still capturing the output of the original model. The various embodiments herein describe embodiments wherein the data-driven approach applied to a multi-scale cellular model of cardiac myofilament (MF) to learn a generative model suitable for cell-to-organ simulations. However, one skilled in the art would understand that the techniques described herein may be applied to various multi-scale models, including non-biological models.

Figure 1A:
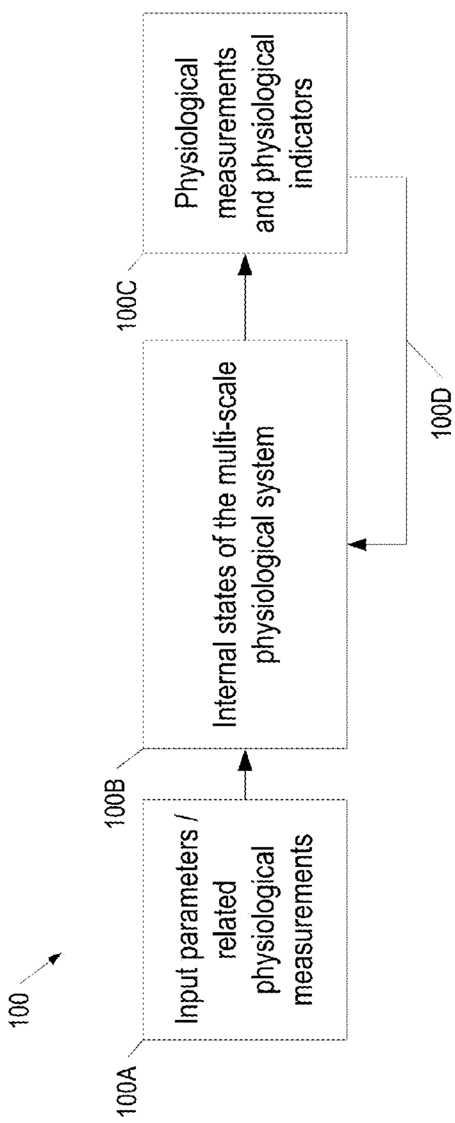
FIG. 1A provides a generic system view of a forward model, as used in some embodiments of the present invention.

FIG. 1A provides a system view of a generic forward model 100, as used in some embodiments of the present invention. The input 100A to the system comprises a set of free constant parameters and/or time varying parameters. In some embodiments, the input 100A includes other physiological measurements related to the physiological measurement of interest. The input parameters are used to update the internal states of a multi-scale physiological system 100B in order to update one or more measureable parameters 100C (e.g., physiological measurements and/or physiological indicators). The model 100 may optionally include a feedback loop 100D to capture changes to one or more output values which result in internal state changes. In some embodiments, the model may be assumed to be in steady-state (i.e., transient phenomena may be neglected) and that at least a portion of the input 100A is fixed or temporally registered. However, in other embodiments, more complex models may be used where these assumptions are not used, the proposed system being generic.

Figure 1B:
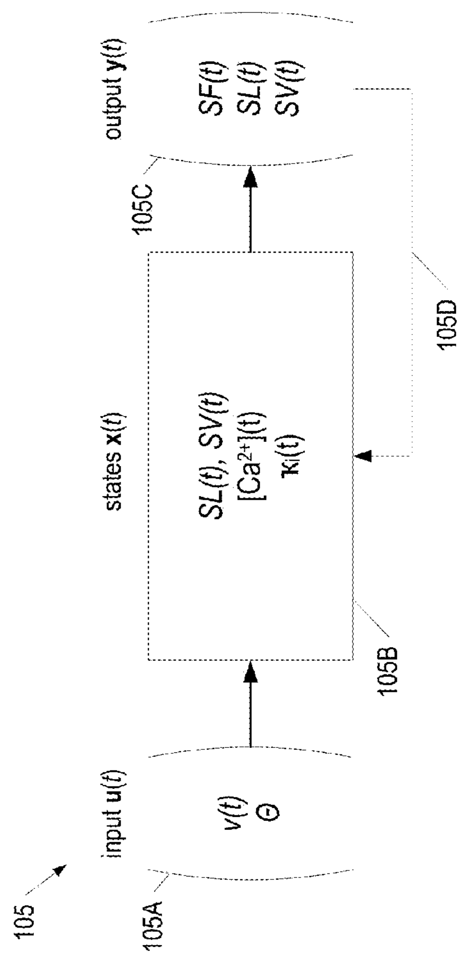
FIG. 1B provides a system view of the forward model described in FIG. 1A applied to model sarcomere force, according to some embodiments of the present invention.

FIG. 1B provides a system view of a forward model 105 of sarcomere force, according to some embodiments of the present invention. More specifically the forward model 105 illustrates how the generic model 100 shown in FIG. 1A may be applied in the example of cardiac modeling. In FIG. 1B, the forward model is based on the J. Rice model of cardiac myofilament (MF). As is understood in the art, the J. Rice model of cardiac myofilament (MF) is designed to capture a wide range of experimental observations. It models the main regulatory processes involved in cross-bridge cycling to compute bulk myoplasmic calcium transient ([Ca2+]), sarcomere length (SL), sarcomere force (SF) and their interdependence throughout the cardiac cycle. From a dynamic system point of view, the input u(t) 105A at time t of the system comprises a set of free constant parameters $\theta \in \mathbb{R}^{n_p}$ (e.g.,related to sub-cellular mechanisms) and a time varying trans-membrane potential v(t), which can be computed using any cellular electrophysiology model. The states of the system x(t) 105B are SL(t) (Sarcomere Length), $[Ca^{2+}](t)$ (calcium concentration), and the numerous transition rates that characterize the cross-bridge cycle, generically denoted as $K_i(t)$ here. The output y(t) 105C is SF(t), SL(t) and SV(t) (Sarcomere Velocity). The model 105 includes a feedback loop 105D to capture changes to SF which result in SL changes. Furthermore, it should be noted that the Rice model 105 presented in FIG. 1B is but one example of a model on which the techniques described herein may be applied. For example, these techniques may be applied to a range of biological multi-scale models including simplified multi-scale models which do not capture molecular pathways, phenomenological models, and detailed models which include a large number of ordinary differential equations (ODEs). These techniques can also be applied to other biological systems (e.g. electrophysiology, energetics, etc.) or non-biological, multi-scale models without modification of the general framework.

Figure 2:
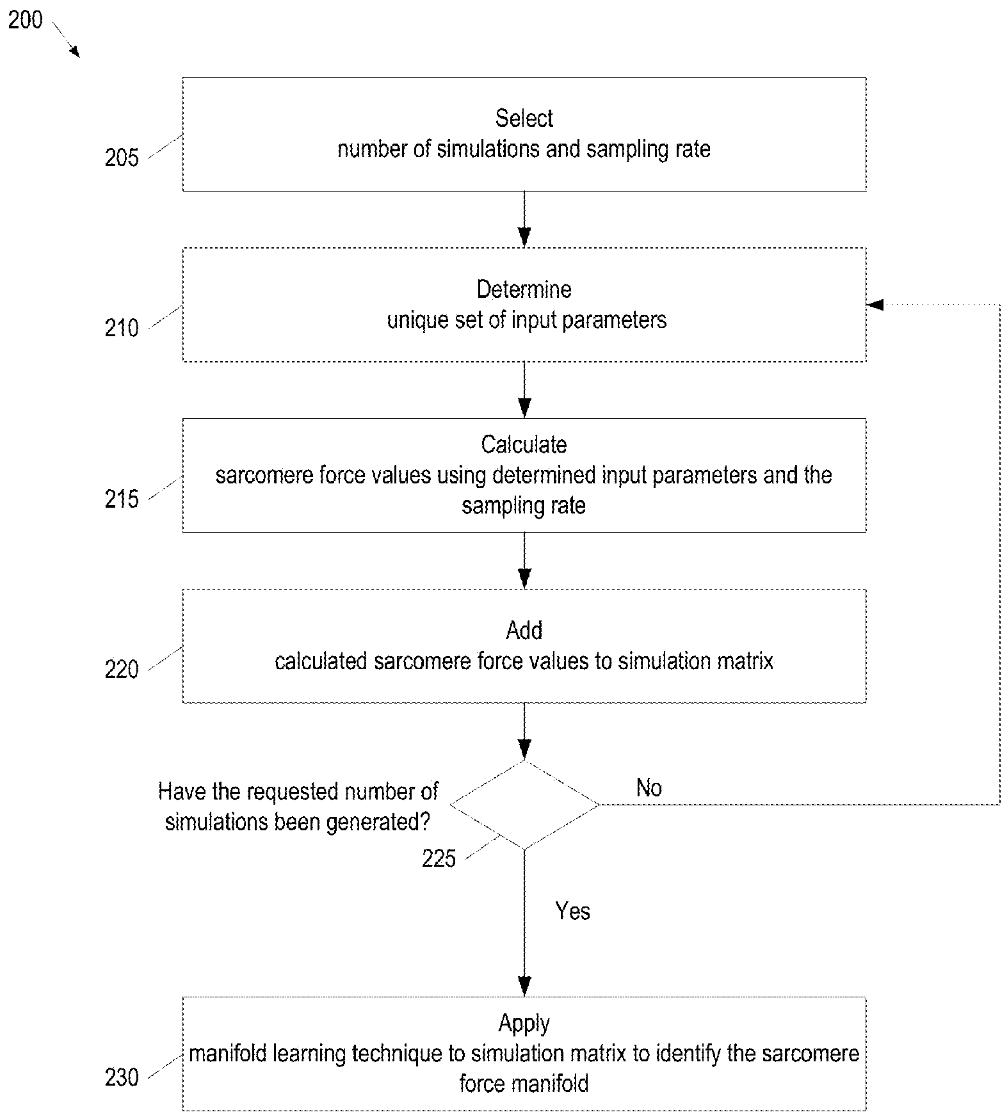
FIG. 2 provides an example of model reduction process, as implemented in some embodiments of the present invention, and applied to analyze components of a forward model.

FIG. 2 provides an example of model reduction process 200, as implemented in some embodiments of the present invention, and applied to analyze components of a forward model. While the example shown in FIG. 2 is applied to a cardiac-based model such as illustrated in FIG. 1B, it should be understood that the process may be generically applied to other models as well. In FIG. 2, the process 200 is used to analyze the dimensionality of the SF manifold $\Omega_{SF}$ . This dimensionality corresponds to the number of intrinsic parameters $n_p$ that are necessary to capture the observed SF(t) (SF(t) being previously computed from the model or measured). At 205, the number of simulations N and the sampling rate $n_s$ are selected, for example, via real-time user selection or retrieval of values that were previously selected by a user. Then, at 210, 215, 220, an iterative process generates SF data for N sets of parameters associated with the model. First, at 210 a unique set of parameters is selected. In some embodiments, the parameters are randomly generated using a range of values for each parameter but constrained to eliminate any non-realistic, non-physiological values. To ensure uniqueness among each simulation, the selected set of parameters may be checked against parameters used for previous simulations. Next, at 215, the selected input parameters and sampling rate are used to calculate sarcomere force values. Specifically, SF is sampled for time values $t \in [t_o, t_{end} = n_s dt]$, where $t_o$, $t_{end}$ and dt are the initial time, the final time and the time step, respectively, of the observed cardiac cycle. The results of the calculations at 215 are stored in a simulation vector which may be defined as $y^i = [SF^i(t_o) \ldots SF^i(t_{end})] \in \mathbb{R}^{n_s}$. At 220, the simulation vector is added to a $N \times n_s$ simulation matrix Y. Then, at 225, a check is made to see if the selected number of simulations has been performed. If additional simulation data is needed, 210, 215, 220 are performed an additional time with a new set of parameters. However, if the selected number of simulations has been performed, the process proceeds to 230 where a manifold learning technique is applied to the simulation matrix to characterize the sarcomere force manifold. The applied manifold learning techniques may include, without limitation, Principal Component Analysis (PCA) and Locally Linear Embedding (LLE), as described in further detail below. It should be noted that the technique is described using sarcomere force as measurement of analysis, but it can applied to any dynamic biological measurement.

In one embodiment, PCA is used to compute the reduced space $\Omega_{SF}^{pca}$ by finding the orthonormal basis formed by the principal components $v_k^T$, $k \in \{1 \ldots n_s\}$, that maximizes the observed covariance. First, a covariance matrix is calculated using each simulation vector y and the simulation matrix Y according to the following equation: $(Y-\bar{y}(Y-\bar{y}),^T)$ where $\bar{y}=1/N\sigma_{i=1}^{N} y^i$. Next, the eigenvectors of the covariance matrix are computed using, for example singular value decomposition (SVD) or any other technique for eigenvector computation technique known in the art. The values for the eigenvectors, ordered by decreasing energy, are the principal components $v_k^T$. Once $v_k^T$ is computed, dimensionality reduction is achieved by first selecting a reduced set of components $v_l^T$, $l \in \{1 \ldots n_q\}$, $n_q \leq n_p << n_s$. Then, the simulation data is projected onto that new space $z_{pca}^i=(y^i-\bar{y},)V$, where V is the matrix $V=(v_1^T \ldots v_{n_q}^T)$. Now, given new PCA coefficients $\hat{z}_{pca}$, the related $\widehat{SF}$ (t) encoded by the vector $\hat{y} \in \Omega_{SF}$ may be reconstructed through $\hat{y}=\bar{y}+\hat{z}_{pca}V$.

Any dimensionality reduction technique can be employed at this stage. For instance, in other embodiments, LLE is used to calculate the low-dimensional space $\Omega_{SF}^{lle}$ that preserves the barycentric coordinates of each data point with respect to its $k_{lee}$ nearest neighbors. Because the mapping is computed using local neighborhoods, the method can capture non-linear manifold structures. The algorithm has three steps: 1) find the $k_{lee}$ nearest neighbors of each data point $y^i$, $\{y^{N^{k_{lee}}(y^i)}\}$, according to the Euclidean distance; 2) compute the barycentric coordinates $w^i$ of $y^i$, with respect to the $k_{lee}$ neighbors; 3) compute embedding coordinates $z_{lle}^i \in \Omega_{SF}^{lle}$ of $n_q \leq n_p << n_s$ dimensions using the barycentric coordinates $w^i$, which amounts to solving an eigenvalue problem. Although LLE does not provide an explicit mapping between $\Omega^{SF}$ and $\Omega_{SF}^{lle}$, it can be extended to new data easily by taking advantage of the preservation of the barycentric coordinates. Let $\hat{y}$ be a new data sample in $\Omega_{SF}$. First, its $k_{lle}$ nearest neighbors within the training set are determined. The barycentric coordinates $\hat{w}$ are calculated and used as interpolation weights to estimate the embedding coordinates $\hat{z}_{lle} \in \Omega_{SF}^{lle}$ from those of the $k_{lle}$ nearest neighbors. New observations of $\hat{y}$ are reconstructed from the embedding coordinates $\hat{z}_{lle}$ in a similar way.

Figure 3:
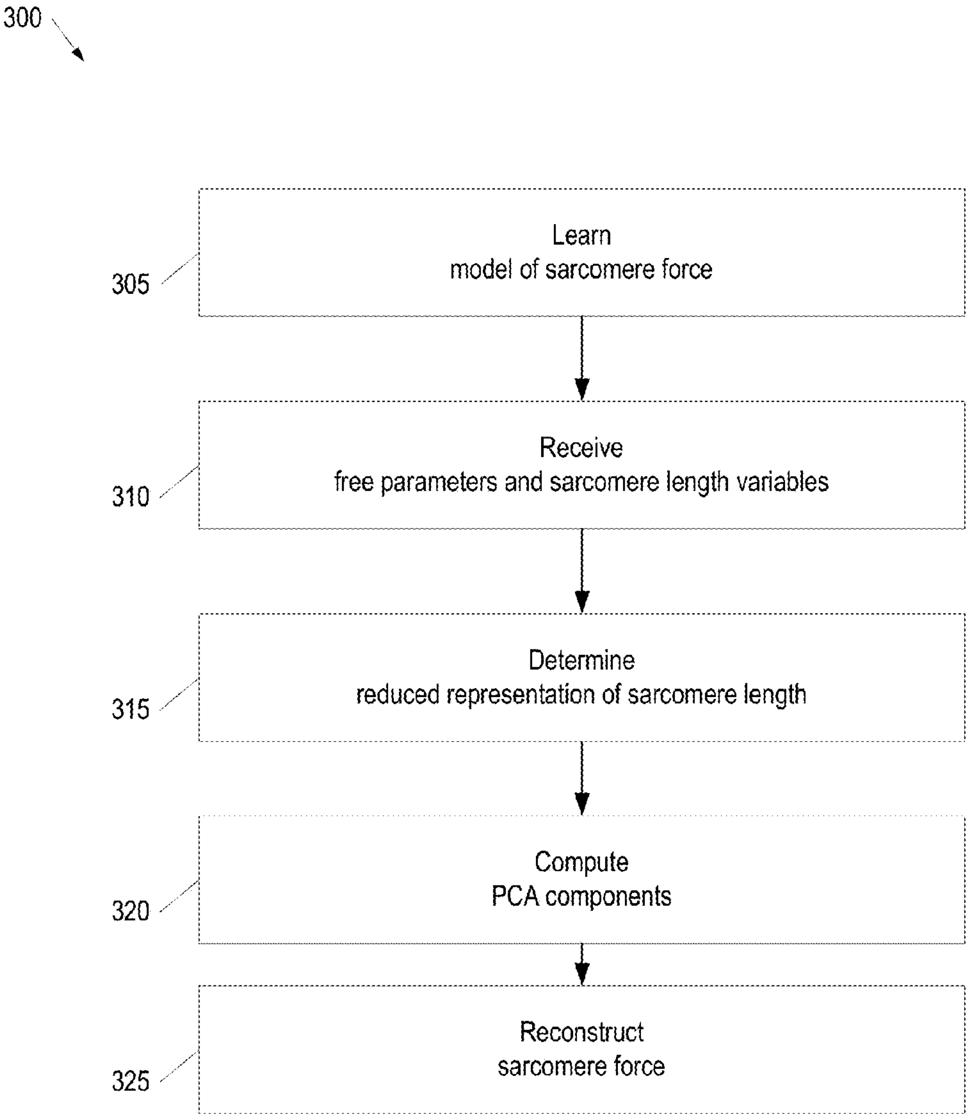
FIG. 3 provides a process for learning a data-driven model to predict sarcomere force, according to some embodiments of the invention.

In the previous step, the proposed framework enabled to identify the intrinsic dimensionality of the multi-scale model. The next step is to learn the forward model itself from the training database. Contrary to direct, explicit models, data-driven models are much more computationally efficient. Furthermore, relevant parameters to the output can automatically be identified during the learning process. FIG. 3 provides a process 300 for learning a data-driven model to predict SF, according to some embodiments of the invention. In the example of FIG. 3, it is assumed that all variables are known throughout the cardiac cycle (static model). The process 400 illustrated in FIG. 4 extends the process 300 of FIG. 3 to predict SF values beyond the current time (dynamic model). At 305, a model f is learned which uses free, constant parameters θ and sarcomere length SL(t) as input. It should be noted that the use of SL(t) is not limiting because SL is an observable state of the system (see FIG. 1). Furthermore, the framework can be extended to any input parameter, being constant or time-varying. In some embodiments, to minimalize correlations between the SL time-points, the input values of SL may be expressed in terms of PCA coefficients $z_{SL} \in \Omega_{SL}^{pca} = \mathbb{R}^{n_{SL}}$, with $n_{SL} \ll n_s$. To optimize model construction, output may be limited to a reduced SF representation. In some embodiments, this reduced SF representation is the embedding coordinates z obtained during model reduction as described previously. Thus, the process 300 illustrated in FIG. 3 may be summarized according to the following equation: $z = f(\theta, z_{SL})$, $f: \mathbb{R}^{n_p} \times \mathbb{R}^{n_{SL}} \rightarrow \mathbb{R}^{n_q}$.

In some embodiments, f is estimated using multivariate adaptive regression splines (MARS), a non-parametric regression method with explicative capabilities. Intuitively, MARS extends linear regression by fitting splines (e.g., linear or cubic) to the predictors to capture data non-linearities and variable interactions. The model may be estimated in two steps. A forward pass fits the splines to the data in a greedy approach such that the mean square error (MSE) on the training set diminishes. The forward pass may construct an overfit model that will not generalize well to new data. Thus, a backward pass is performed, which removes terms with the smallest increase in residual MSE. This step, similar to the model selection techniques in linear regression, enables one to identify the most relevant responses in the model, thus providing indications on the input parameters that have most impact on SF dynamics. In some embodiments, f is estimated component-wise, i.e. $f = [f_1 \ldots f_{n_q}]$, the $f_{k \in \{1 \ldots n_q\}}: \mathbb{R}^{n_p} \times \mathbb{R}^{n_{SL}} \rightarrow \mathbb{R}^{n_q}$ being $n_q$ independent MARS models. It should be noted at this stage that any regression algorithm could be employed at this stage, including but not limited to linear regression, LS BOOST regression, etc.

Continuing with reference to FIG. 3, at 310, new values for free parameters $\hat{\theta}$ and $\widehat{SL}(t)$ are received. Next, at 315, $\widehat{SL}(t)$ is projected onto $\overleftrightarrow{\Omega_{SL}^{pca}}$ to compute its representation $\hat{z}_{SL}$. Then, at 320, the PCA coefficients are computed according to $\hat{z} = f(\hat{\theta}, \hat{z}_{SL})$. Although steps 315 and 320 have been described with respect to PCA, it should be noted that other manifold learning techniques may be used as well. For example, in some embodiments, $\widehat{SL}(t)$ is projected onto $\Omega_{SL}^{lle}$ at 315 and embedding coefficients are used computed at 320. Returning to FIG. 3, at 325, $\hat{z}$ is used to reconstruct the SF curve $\hat{y}$ using the techniques discussed above with reference to process 200 of FIG. 2. For example, in embodiments wherein PCA is used as the manifold learning technique, the related $\widehat{SF}(t)$ encoded by the vector $\hat{y} \in \Omega_{SF}$ may be reconstructed through $\hat{y} = \bar{y} + \hat{z}_{pca} V$, with $\bar{y}$ representing the mean SF values for a training set and V representing a reduced set of the eigenvectors included in a covariance matrix of the training data set.

Figure 4:
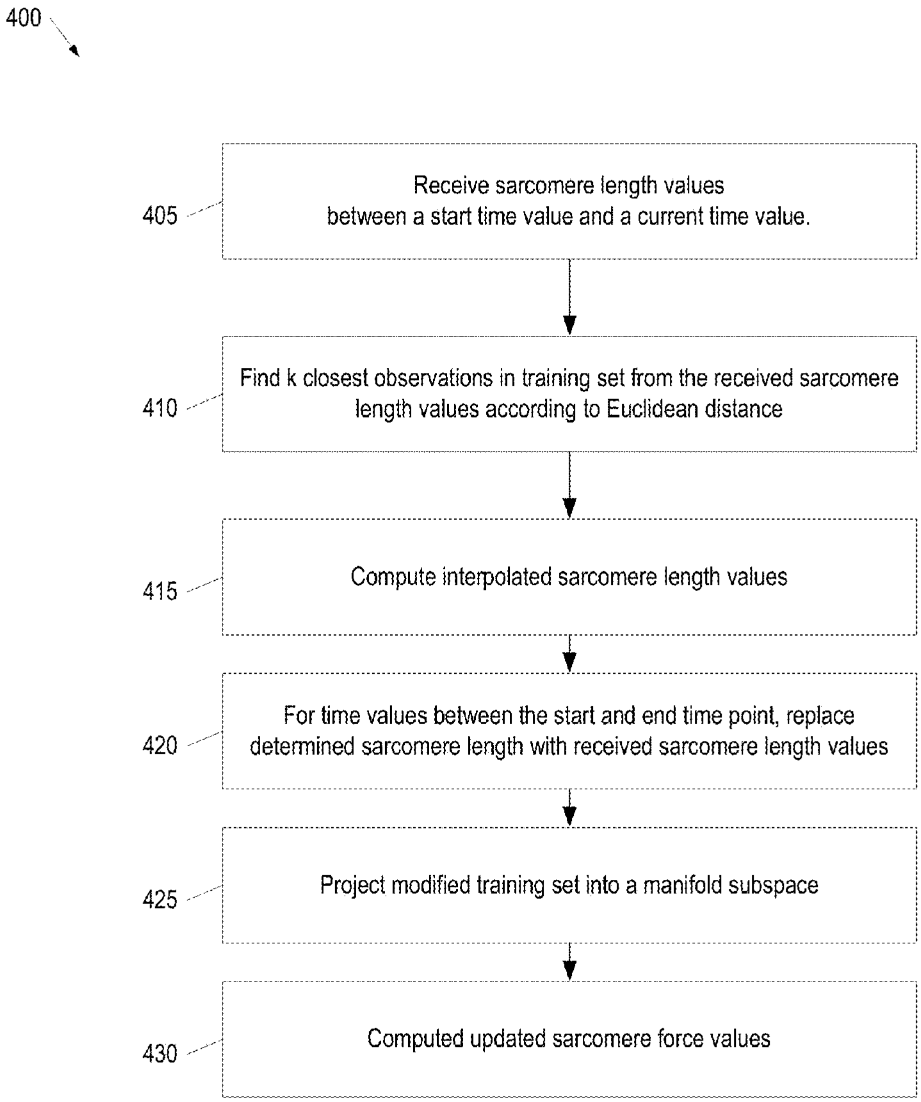
FIG. 4 provides process for extending the process described in FIG. 3 to dynamic scenarios, according to some embodiments of the present invention.

In practice, sarcomere length SL(t) is only known for values of t between an initial time $t_0$ and a current time $t_c$. FIG. 4 provides process 400 for extending the process described in FIG. 3 to dynamic scenarios to predict SF beyond $t_c$, according to some embodiments of the present invention. More specifically, the example process 400 of FIG. 4 extends the data driven model discussed herein to applications where past SL dynamics may be used to find the closest candidates on the SL manifold. These candidates may then be used to predict the entire SL dynamics, which is utilized as input to the previously learned data-driven forward model to compute SF at the next time steps. Let $x_{SL}$ be the vector of dimension $n_{t_c} < n_s$ that encodes SL(t), $t \in [t_0, t_c]$. At 405, $x_{SL}$ is received along with a set of free constant parameters θ. Next, at 410, the k closest SL dynamics within the training set from $x_{SL}$ are determined based on based on the Euclidean distance computed between $t_0$ and $t_c$. It should be noted that other distances, which take for instance into account the topology of the manifold, could be employed. Next, at 415, $x_{SL_{train}}$ is determined by interpolating from the k samples, weighted by their respective distance, over the entire cycle. At 420, the values of $x_{SL_{train}}$ between $t = [t_0; t_c]$ are replaced by those of the actual $x_{SL}$ to yield a modified training set $x_{SL_{input}}$. Then, at 425, $x_{SL_{input}}$ is projected into the SL subspace (e.g., $\Omega_{SF}^{pca}$) to determine the predicted values $z_{SL}$. Finally, at 430, $z = [f(\theta, z_{SL})$ is computed and SF may be reconstructed from z to determine $SF(t_c+dt)$. In turn, $SF(t_c+dt)$ may be used to calculate $SL(t_c+dt)$, for example, according to the constitutive law of the whole-heart model. The process 400 may be iterated throughout time-steps to compute the entire SF dynamics.

It should be noted that the framework described herein is generic. Thus, in some embodiments, techniques such as partial least squares (PLS), kernel methods, boosting trees, and/or neural networks could also be used to 1) reduce model dimensionality instead of PCA and LLE and 2) to learn the forward model instead of MARS.

In some embodiments, the systems, methods, and apparatuses described herein are integrated into a multi-scale whole-heart model. For example, in one embodiment, from the data-driven model (see, e.g., FIG. 3), the effective active stress is computed to apply to the nodes of a 3D mesh representing the heart. The mesh would then deform according to a constitutive law and various boundary conditions. At each time step, the sarcomere length may be estimated by calculating the strain along the fiber orientation. The new sarcomere length may then be used as input to the data-driven model (see, e.g., FIG. 4), to compute the new active stress. In some embodiments, the data-driven model is linked molecular information with organ-level phenotypes. Molecular information may be used to modify the data-driven model parameters. Then, using the dynamic data-driven model (see, e.g., FIG. 4), changes in organ phenotype may be inferred.

Figure 5:
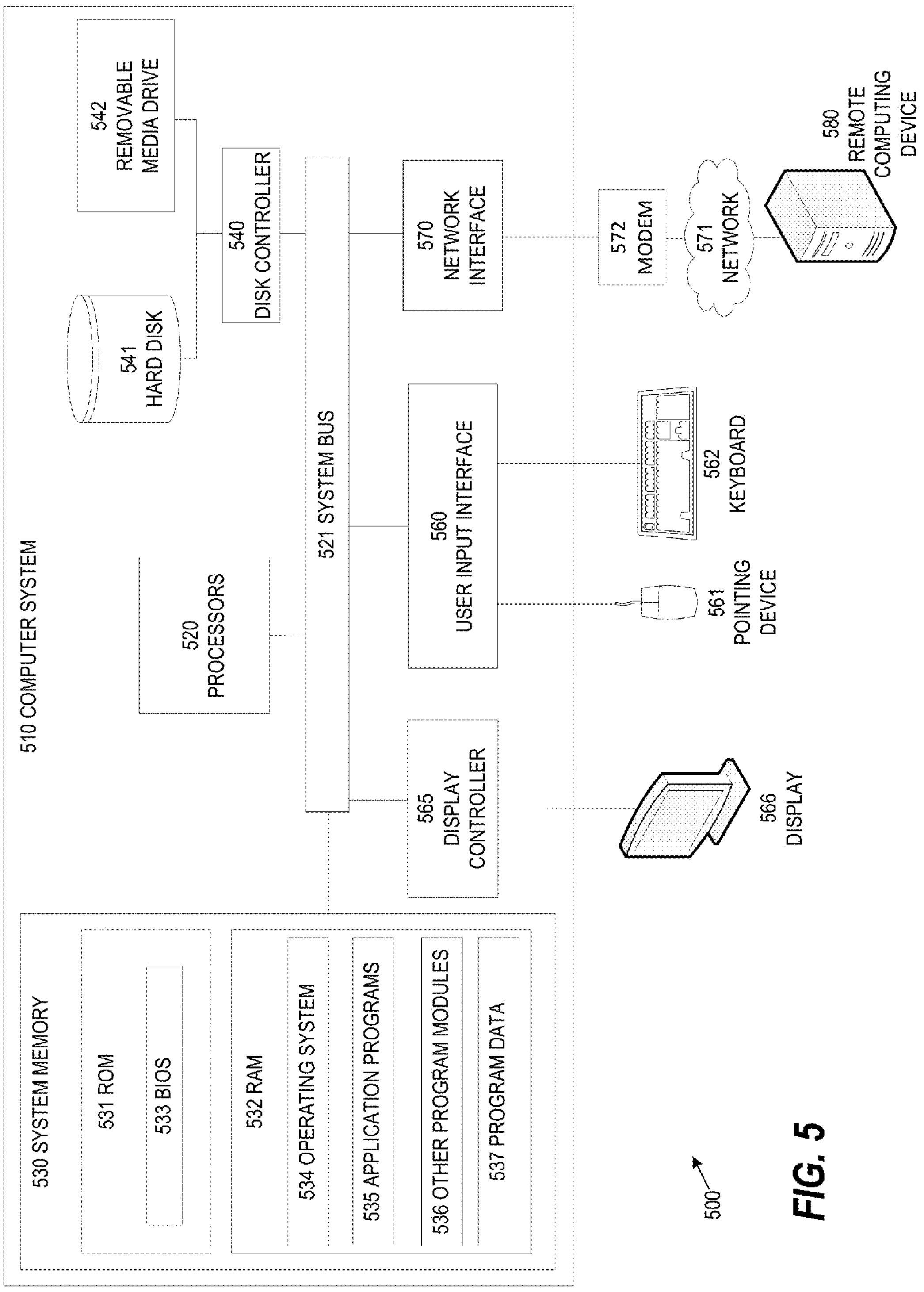
FIG. 5 illustrates an exemplary computing environment within which embodiments of the invention may be implemented.

FIG. 5 illustrates an exemplary computing environment 500 within which embodiments of the invention may be implemented. This environment 500 may be used, for example, to execute system and processes described in FIGS. 1-4. Computing environment 500 may include computer system 510, which is one example of a computing system upon which embodiments of the invention may be implemented. Computers and computing environments, such as computer system 510 and computing environment 500, are known to those of skill in the art and thus are described briefly here.

As shown in FIG. 5, the computer system 510 may include a communication mechanism such as a bus 521 or other communication mechanism for communicating information within the computer system 510. The system 510 further includes one or more processors 520 coupled with the bus 521 for processing the information.

The processors 520 may include one or more central processing units (CPUs), graphical processing units (GPUs), or any other processor known in the art. More generally, a processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting, or transmitting information for use by an executable procedure or an information device, and/or by routing the information to an output device. A processor may use or comprise the capabilities of a computer, controller or microprocessor, for example, and be conditioned using executable instructions to perform special purpose functions not performed by a general purpose computer. For example, in some embodiments, a modeling processor is used in combination with a receiver module and a database. This modeling processor may be configured to perform one or more of the methods described herein. A processor may be coupled (electrically and/or as comprising executable components) with any other processor enabling interaction and/or communication there-between. A user interface processor or generator is an element comprising electronic circuitry or software or a combination of both for generating display images or portions thereof. A user interface comprises one or more display images enabling user interaction with a processor or other device.

Continuing with reference to FIG. 5, the computer system 510 also includes a system memory 530 coupled to the bus 521 for storing information and instructions to be executed by processors 520. The system memory 530 may include computer readable storage media in the form of volatile and/or nonvolatile memory, such as read only memory (ROM) 531 and/or random access memory (RAM) 532. The system memory RAM 532 may include other dynamic storage device(s) (e.g., dynamic RAM, static RAM, and synchronous DRAM). The system memory ROM 531 may include other static storage device(s) (e.g., programmable ROM, erasable PROM, and electrically erasable PROM). In addition, the system memory 530 may be used for storing temporary variables or other intermediate information during the execution of instructions by the processors 520. A basic input/output system 533 (BIOS) containing the basic routines that help to transfer information between elements within computer system 510, such as during start-up, may be stored in ROM 531. RAM 532 may contain data and/or program modules that are immediately accessible to and/or presently being operated on by the processors 520. System memory 530 may additionally include, for example, operating system 534, application programs 535, other program modules 536 and program data 537.

The computer system 510 also includes a disk controller 540 coupled to the bus 521 to control one or more storage devices for storing information and instructions, such as a magnetic hard disk 541 and a removable media drive 542 (e.g., floppy disk drive, compact disc drive, tape drive, and/or solid state drive). The storage devices may be added to the computer system 510 using an appropriate device interface (e.g., a small computer system interface (SCSI), integrated device electronics (IDE), Universal Serial Bus (USB), or FireWire).

The computer system 510 may also include a display controller 565 coupled to the bus 521 to control a display or monitor 565, such as a cathode ray tube (CRT) or liquid crystal display (LCD), for displaying information to a computer user. The computer system includes an input interface 560 and one or more input devices, such as a keyboard 561 and a pointing device 562, for interacting with a computer user and providing information to the processor 520. The pointing device 562, for example, may be a mouse, a light pen, a trackball, or a pointing stick for communicating direction information and command selections to the processor 520 and for controlling cursor movement on the display 566. The display 566 may provide a touch screen interface which allows input to supplement or replace the communication of direction information and command selections by the pointing device 561.

The computer system 510 may perform a portion or all of the processing steps of embodiments of the invention in response to the processors 520 executing one or more sequences of one or more instructions contained in a memory, such as the system memory 530. Such instructions may be read into the system memory 530 from another computer readable medium, such as a hard disk 541 or a removable media drive 542. The hard disk 541 may contain one or more datastores and data files used by embodiments of the present invention. Datastore contents and data files may be encrypted to improve security. The processors 520 may also be employed in a multi-processing arrangement to execute the one or more sequences of instructions contained in system memory 530. In alternative embodiments, hard-wired circuitry may be used in place of or in combination with software instructions. Thus, embodiments are not limited to any specific combination of hardware circuitry and software.

As stated above, the computer system 510 may include at least one computer readable medium or memory for holding instructions programmed according embodiments of the invention and for containing data structures, tables, records, or other data described herein. The term "computer readable medium" as used herein refers to any medium that participates in providing instructions to the processor 520 for execution. A computer readable medium may take many forms including, but not limited to, non-transitory, nonvolatile media, volatile media, and transmission media. Non-limiting examples of nonvolatile media include optical disks, solid state drives, magnetic disks, and magneto-optical disks, such as hard disk 541 or removable media drive 542. Non-limiting examples of volatile media include dynamic memory, such as system memory 530. Non-limiting examples of transmission media include coaxial cables, copper wire, and fiber optics, including the wires that make up the bus 521. Transmission media may also take the form of acoustic or light waves, such as those generated during radio wave and infrared data communications.

The computing environment 500 may further include the computer system 520 operating in a networked environment using logical connections to one or more remote computers, such as remote computer 580. Remote computer 580 may be a personal computer (laptop or desktop), a mobile device, a server, a router, a network PC, a peer device or other common network node, and typically includes many or all of the elements described above relative to computer 510. When used in a networking environment, computer 510 may include modem 572 for establishing communications over a network 571, such as the Internet. Modem 572 may be connected to system bus 521 via user network interface 570, or via another appropriate mechanism.

Network 571 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 510 and other computers (e.g., remote computing system 580). The network 571 may be wired, wireless or a combination thereof. Wired connections may be implemented using Ethernet, Universal Serial Bus (USB), RJ-11, or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 571.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. In some embodiments, a hardware or software component is specifically configured to facilitate the receipt of data (e.g., a "receiver module").

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the UI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The embodiments of the present invention can be included in an article of manufacture comprising, for example, a non-transitory computer readable medium. This computer readable medium may have embodied therein a method for facilitating one or more of the techniques utilized by some embodiments of the present invention. The article of manufacture may be included as part of a computer system or sold separately.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A method of computing physiological measurements resulting from a multi-scale system using a data-driven model, the method comprising:

generating a database of physiological measurements associated with a multi-scale physiological system;

using, by a computer, dimensionality reduction techniques on the database to identify a reduced set of components explaining the multi-scale physiological system;

learning, by the computer, a data-driven model of the multi-scale physiological system from the database according to a process comprising:

receiving a plurality of related physiological measurement values corresponding to times between a start time value and a current time value, selecting a subset of simulated physiological measurement vectors from the database, creating an interpolated related physiological measurement vector based on the subset of simulated physiological measurement vectors and the related physiological measurement values, and projecting the interpolated related physiological measurement vector onto a manifold space to yield a plurality of related physiological measurement manifold coefficients;

receiving, by the computer, new input parameters;

computing, by the computer, new physiological measurements from the new input parameters based on the plurality of related physiological measurement manifold coefficients, using the data-driven model;

computing, by the computer, new derived physiological indicators based on the reduced set of components; and displaying at least one of the new physiological measurements and the new derived physiological indicators.

2. The method of claim 1, wherein generating the database of physiological measurements associated with the multi-scale physiological system comprises:

selecting a number of simulations and a sampling rate; and performing a training data creation process a number of times equal to the number of simulations, the training data creation process comprising:

determining a plurality of unique input parameters, using the unique input parameters, sampling rate, and a multi-scale model of a respective physiological item associated with the multi-scale physiological system to calculate a plurality of values associated with the respective physiological item, and adding the calculated values to the database.

3. The method of claim 1, wherein the database comprises experimental measurements of the multi-scale physiological system.

4. The method of claim 1, wherein using dimensionality reduction techniques on the database to identify the reduced set of components explaining the multi-scale physiological system comprises:

applying a manifold learning technique to the database to identify the reduced set of components.

5. The method of claim 4, wherein the manifold learning technique is Principle Component Analysis (PCA) and the reduced set of components comprises PCA coefficients.

6. The method of claim 4, wherein the manifold learning technique is Locally Linear Embedding (LLE) and the reduced set of components comprises embedding coordinates.

7. The method of claim 1, wherein learning the data-driven model of the multi-scale physiological system from the database comprises:

selecting one or more related physiological measurements from the database; and projecting the one or more related physiological measurements onto a manifold space to yield a reduced representation of each related physiological measurement, wherein the data-driven model is a statistical model relating the new input parameters and the reduced representation of the one or more related physiological measurements with the new physiological measurements.

8. The method of claim 7, wherein the new physiological measurements correspond to sarcomere force and the related physiological measurements correspond to sarcomere length.

9. The method of claim 1, wherein computing the new physiological measurements from the new input parameters based on the plurality of related physiological measurement manifold coefficients, using the data-driven model, comprises:

applying the data-driven model to the related physiological measurement manifold coefficients and the new input parameters to yield a plurality of output physiological measurement manifold coefficients; and determining the new multi-scale physiological measurements based on the output physiological measurement manifold coefficients.

10. The method of claim 1, wherein selecting the subset of simulated physiological measurement vectors from the database comprises:

for each simulated related physiological measurement vector in the database, determining a distance value between a respective related simulated physiological measurement vector and the received related physiological measurement values between the start time and the current time value;

identifying a predetermined number of simulated related physiological measurement vectors in the database as being closest to the received related physiological measurement values based on their respective determined distance values; and designating the predetermined number of simulated related physiological measurement vectors as the selected subset of simulated physiological measurement vectors.

11. The method of claim 10, wherein creating the interpolated related physiological measurement vector based on the subset of simulated physiological measurement vectors and the related physiological measurement values comprises:

determining an interpolated related physiological measurement vector by interpolating the subset of the simulated related physiological measurement vectors over a heart cycle, weighting each of simulated related physiological measurement vectors in the subset of simulated related physiological measurement by its respective distance value; and replacing interpolated related physiological measurement values in the initial interpolated related physiological measurement vector between the start time value and the current time value with corresponding related measured physiological measurement values to yield the related physiological measurement vector.

12. An article of manufacture for computing physiological measurements using a data-driven model, the article of manufacture comprising a non-transitory computer-readable medium holding computer-executable instructions for performing a method comprising:

generating a database of physiological measurements associated with a multi-scale physiological system;

using dimensionality reduction techniques on the database to identify a reduced set of components explaining the physiological system;

learning a data-driven model of the physiological system from the database according to a process comprising:

receiving a plurality of related physiological measurement values corresponding to times between a start time value and a current time value, selecting a subset of simulated physiological measurement vectors from the database, creating an interpolated related physiological measurement vector based on the subset of simulated physiological measurement vectors and the related physiological measurement values, and projecting the interpolated related physiological measurement vector onto a manifold space to yield a plurality of related physiological measurement manifold coefficients;

receiving new input parameters;

computing new multi-scale physiological measurements from the new input parameters based on the plurality of related physiological measurement manifold coefficients, using the data-driven model;

computing new derived physiological indicators based on the reduced set of components; and displaying at least one of the new physiological measurements and the new derived physiological indicators.

13. The article of manufacture of claim 12, wherein generating the database of physiological measurements associated with the physiological system comprises:

selecting a number of simulations and a sampling rate; and performing a training data creation process a number of times equal to the number of simulations, the training data creation process comprising:

determining a plurality of unique input parameters, using the unique input parameters, sampling rate, and a multi-scale model of a respective physiological item associated with the multi-scale physiological system to calculate a plurality of values associated with the respective physiological item, and adding the calculated values to the database.

14. The article of manufacture of claim 12, wherein learning the data-driven model of the multi-scale physiological system from the database comprises:

selecting one or more related physiological measurements from the database; and projecting the one or more related physiological measurements onto a manifold space to yield a reduced representation of each related physiological measurement, wherein the data-driven model is a statistical model relating the new input parameters and the reduced representation of the one or more related physiological measurements with the new physiological measurements.

15. The article of manufacture of claim 12, wherein computing the new physiological measurements from the new input parameters based on the plurality of related physiological measurement manifold coefficients, using the data-driven model comprises:

applying the data-driven model to the related physiological measurement manifold coefficients and the new input parameters to yield a plurality of output physiological measurement manifold coefficients; and determining the new multi-scale physiological measurement based on the output physiological measurement manifold coefficients.

16. A system for computing multi-scale, physiological measurements using a data-driven model, the system comprising:

a receiver module configured to receiving new input parameters;

a database configured to store physiological measurements associated with a multi-scale physiological system;

a modeling processor configured to:

use dimensionality reduction techniques on the database to identify a reduced set of components explaining the multi-scale physiological system, learn a data-driven model of the multi-scale physiological system from the database according to a process comprising:

receiving a plurality of related physiological measurement values corresponding to times between a start time value and a current time value, selecting a subset of simulated physiological measurement vectors from the database, creating an interpolated related physiological measurement vector based on the subset of simulated physiological measurement vectors and the related physiological measurement values, and projecting the interpolated related physiological measurement vector onto a manifold space to yield a plurality of related physiological measurement manifold coefficients, receive new input parameters, compute new physiological measurements from the new input parameters based on the plurality of related physiological measurement manifold coefficients, using the data-driven model, compute new derived physiological indicators based on the reduced set of components, and display at least one of the new physiological measurements and the new derived physiological indicators.

17. The system of claim 16, wherein the modeling processor is configured to learn the data-driven model of the multi-scale physiological system from the database by a process comprising:

selecting one or more related physiological measurements from the database; and projecting the one or more related physiological measurements onto a manifold space to yield a reduced representation of each related physiological measurement, wherein the data-driven model is a statistical model relating the new input parameters and the reduced representation of the one or more related physiological measurements with the new physiological measurements.

18. The system of claim 16, wherein the modeling processor is configured to compute new multi-scale physiological measurement from the new input parameters, using the data-driven model and the reduced set of components by a process comprising:

applying the data-driven model to the related physiological measurement manifold coefficients and the new input parameters to yield a plurality of output physiological measurement manifold coefficients; and determining the new multi-scale physiological measurement based on the output physiological measurement manifold coefficients.

* * * * *